(12) United States Patent
Nadkarni et al.

(10) Patent No.: US 11,101,021 B2
(45) Date of Patent: Aug. 24, 2021

(54) ELECTRONIC PHENOTYPING TECHNIQUE FOR DIAGNOSING CHRONIC KIDNEY DISEASE

(71) Applicant: Icahn School of Medicine at Mount Sinai, New York, NY (US)

(72) Inventors: Girish Nadkarni, New York, NY (US); Omri Gottesman, New York, NY (US); Stephen Bartlett Ellis, Long Island City, NY (US); Erwin Bottinger, New Rochelle, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 489 days.

(21) Appl. No.: 15/502,243

(22) PCT Filed: Jul. 31, 2015

(86) PCT No.: PCT/US2015/043317
§ 371 (c)(1),
(2) Date: Feb. 7, 2017

(87) PCT Pub. No.: WO2016/022437
PCT Pub. Date: Feb. 11, 2016

(65) Prior Publication Data
US 2017/0228506 A1 Aug. 10, 2017

Related U.S. Application Data

(60) Provisional application No. 62/035,141, filed on Aug. 8, 2014.

(51) Int. Cl.
G06Q 50/00 (2012.01)
A61B 5/00 (2006.01)
(Continued)

(52) U.S. Cl.
CPC .............. *G16H 10/60* (2018.01); *A61B 5/201* (2013.01); *A61B 5/7275* (2013.01); *G06F 19/00* (2013.01); *G16H 50/20* (2018.01); *A61B 2218/00* (2013.01)

(58) Field of Classification Search
CPC ... C12Q 1/6883; G06F 19/3456; G06F 19/00; G06F 16/285; G06F 19/3418;
(Continued)

(56) References Cited

U.S. PATENT DOCUMENTS

2009/0299645 A1* 12/2009 Colby .................. C12Q 1/6883
702/19
2013/0236981 A1 9/2013 Haick et al.
(Continued)

FOREIGN PATENT DOCUMENTS

WO 2014/089022 6/2014
WO 2015/070041 5/2015

OTHER PUBLICATIONS

Nadkarni, et al., "Development and validation of an electronic phenotyping algorithm for chronic kidney disease," Nov. 14, 2014, AMIA Annu Symp Proc., pp. 907-916.
(Continued)

*Primary Examiner* — Maroun P Kanaan
(74) *Attorney, Agent, or Firm* — Fish & Richardson P.C.

(57) ABSTRACT

An example method of diagnosing chronic kidney disease (CKD) includes obtaining an electronic medical record for a patient having medical data. The medical data includes an indication if the patient had been previously diagnosed with CKD, an indication if the patient had previously undergone a kidney transplant, an indication if the patient had previously undergone a renal dialysis procedure, an indication if the patient had previously been diagnosed with another type of kidney disease, one or more glomerular filtration rate
(Continued)

(GFR) measurements associated with the patient, an indication if the patient has type 2 diabetes, and/or an indication if the patient has hypertension. The method also includes automatically determining that the patient has CKD or does not have CKD based on the medical data in the electronic record.

10 Claims, 8 Drawing Sheets

(51) Int. Cl.
   *G16H 10/60*    (2018.01)
   *G16H 50/20*    (2018.01)
   *G06F 19/00*    (2018.01)
   *A61B 5/20*     (2006.01)

(58) Field of Classification Search
   CPC .... G06F 16/2282; G16H 50/30; G16H 10/60; G16H 50/20; G16H 50/70; G16H 40/67; G06Q 50/24
   See application file for complete search history.

(56) References Cited

U.S. PATENT DOCUMENTS

2014/0350954 A1    11/2014    Ellis et al.
2015/0037325 A1*   2/2015     Lu ................... C07K 14/70503
                                                         424/133.1

OTHER PUBLICATIONS

Huopaniemi, et al., "Disease progression subtype discovery from longitudinal EMR data with a majority of missing values and unknown initial time points," Nov. 14, 2014, AMIA Annu Symp Proc., pp. 709-713.

Mendu, et al., "Implementation of a CKD checklist for primary care providers," Aug. 18, 2014, Clin J Am Soc Nephrol., vol. 9, pp. 1526-1535.

International Search Report issued by ISA/US dated Nov. 9, 2015, for PCT/US2015/043317.

* cited by examiner

ELECTRONIC PHENOTYPING TECHNIQUE FOR DIAGNOSING CHRONIC KIDNEY DISEASE

GOVERNMENT CLAUSE

This invention was made with government support under U01HG006380 awarded by The National Institutes of Health. The government has certain rights in the invention.

TECHNICAL FIELD

This disclosure relates to automated medical diagnoses, and more particularly to automatically making medical diagnoses using phenotypic analysis.

BACKGROUND

Chronic kidney disease is a common and complex disease affecting approximately 26 million American adults. It is rising in prevalence with high public health costs and is associated with a high degree of morbidity and mortality. Reduced estimated glomerular filtration rate (e.g., eGFR or GFR) is a well-accepted risk factor for all-cause mortality including cardiovascular mortality. Further, adjusted rates of all-cause mortality are 6.5-7.4 times greater for dialysis patients than for individuals in the general population. Among the US population, recent studies have estimated the overall lifetime risk of developing CKD stage 3 to be 59%. Diabetes and hypertension are the predominant causes of CKD, accounting for approximately 44% and 30% of incident CKD cases. As CKD is a significant health problem, accurate identification of diabetic and/or hypertensive CKD cases and controls for both research and clinical purposes is imperative.

Accurate identification of individuals satisfying specific criteria (cases and controls) from a large institutional population allows us to enroll for randomized trials, predict/track outcomes/progression, and perform retrospective cohort studies. In many cases, studying the progression of complex diseases such as CKD is difficult as the recruitment of cohorts is a laborious process that creates a bottleneck in both clinical and translational research. In order to streamline this process, there has been an impetus to create databases of biological samples (e.g., "biobanks") to enroll individuals in medical care settings. The push from healthcare regulatory agencies for electronic medical records (EMRs) that provide a large amount of information available for research purposes has also been integral in improving the formation of research cohorts. With appropriate patient consent and de-identifying data, the EMRs of patients are available and allow the studying of evolution and progression of disease. In clinical care settings, a wealth of data is available through ICD-9 codes, discrete laboratory results, test reports, patient demographics, and notes written by the treating physicians. All of these data are available in a longitudinal form with multiple patient visits over several years.

Electronic medical records (EMR) can provide a variety of clinical data collected during routine clinical care encounters. In some cases, EMR can contain a collection of longitudinal phenotypic data that potentially offers valuable information for discovering clinical population subtypes, and can potentially be used in association studies in medical research and in the prediction of outcomes in patient care. In many cases, a number of clinical parameters and laboratory tests are collected as part of routine clinical care and their results are stored in an EMR (e.g., in electronic records stored in a data warehouse). Collections of EMRs can thus represent a general patient population, and can be used for a variety of statistical analyses. As examples, routinely collected data includes systolic blood pressure (SBP), low-density lipoproteins (LDL), high-density lipoproteins (HDL), triglycerides, hemoglobin A1C (marker for diabetes and diabetes (blood glucose) control), and estimated glomerular filtration rate (eGFR; a marker of kidney function).

In the fields of medical research and clinical care, there is interest in discovering groups of similar patients with similar disease progression patterns. For example, groups of similar patients can be determined for metabolic syndromes that involve varying accumulation of obesity, hypertension, hyperlipidemia, Type 2 diabetes, coronary artery disease and chronic kidney disease (CKD). Information about each of these groups can be used to provide improved medical diagnoses of current and future patients, provide more accurate predictions of patient outcome, and improve the overall quality of clinical care.

SUMMARY

In general, in an aspect, a method of diagnosing chronic kidney disease (CKD) includes obtaining an electronic medical record for a patient having medical data. The electronic medical record includes an indication if the patient had been previously diagnosed with CKD, an indication if the patient had previously undergone a kidney transplant, an indication if the patient had previously undergone a renal dialysis procedure, an indication if the patient had previously been diagnosed with another type of kidney disease, one or more glomerular filtration rate (GFR) measurements associated with the patient, an indication if the patient has type 2 diabetes, and/or an indication if the patient has hypertension. The method also includes automatically determining that the patient has CKD or does not have CKD based on the medical data in the electronic record. The details of one or more implementations are set forth in the accompanying drawings and the description below. Other features and advantages will be apparent from the description and drawings, and from the claims.

Implementations of this aspect may include one or more of the following features:

In some implementations, the step of automatically determining that the patient has CKD includes determining whether the patient has diabetic CKD, has diabetic/hypertensive CKD, has hypertensive CKD, or does not have CKD. In some implementations, the step of automatically determining that the patient has diabetic CKD, has diabetic/hypertensive CKD, has hypertensive CKD, or does not have CKD is further based on one or more exclusion criterion.

In general, in another aspect, a method of diagnosing chronic kidney disease (CKD) includes creating an electronic medical record for a patient having medical data comprising one or more data items. The electronic medical record includes an indication if the patient had been previously diagnosed with CKD, an indication if the patient had previously undergone a kidney transplant, an indication if the patient had previously undergone a renal dialysis procedure, an indication if the patient had previously been diagnosed with another type of kidney disease, one or more glomerular filtration rate (GFR) measurements associated with the patient, an indication if the patient has type 2 diabetes, and/or an indication if the patient has hypertension. The method also includes excluding a patient if one or more exclusion criteria are met, and automatically diagnosing a patient as having CKD based on the electronic medical record, wherein the patient is diagnosed as having diabetic CKD, diabetic/hypertensive CKD, or hypertensive CKD.

In general, in another aspect, a system for diagnosing chronic kidney disease (CKD) includes a computing apparatus configured to obtain an electronic medical record for a patient having medical data. The electronic medical record includes an indication if the patient had been previously diagnosed with CKD, an indication if the patient had previously undergone a kidney transplant, an indication if the patient had previously undergone a renal dialysis procedure, an indication if the patient had previously been diagnosed with another type of kidney disease, one or more glomerular filtration rate (GFR) measurements associated with the patient, an indication if the patient has type 2 diabetes, and/or an indication if the patient has hypertension. The computing apparatus is also configured to automatically determine that the patient has CKD or does not have CKD based on the medical data in the electronic record.

Implementations of this aspect may include one or more of the following features:

In some implementations, the computing system is configured to automatically determine that the patient has CKD by determining whether the patient has diabetic CKD, has diabetic/hypertensive CKD, has hypertensive CKD, or does not have CKD. In some implementations, the computing system is configured to automatically determine that the patient has diabetic CKD, has diabetic/hypertensive CKD, has hypertensive CKD, or does not have CKD based on one or more exclusion criterion.

In general, in another aspect, a non-transitory computer readable medium stores instructions that are operable when executed by a data processing apparatus to perform operations for determining a permeability of a subterranean formation. The operations include obtaining an electronic medical record for a patient having medical data. The medical record includes an indication if the patient had been previously diagnosed with CKD, an indication if the patient had previously undergone a kidney transplant, an indication if the patient had previously undergone a renal dialysis procedure, an indication if the patient had previously been diagnosed with another type of kidney disease, one or more glomerular filtration rate (GFR) measurements associated with the patient, an indication if the patient has type 2 diabetes, and/or an indication if the patient has hypertension. The operations also include automatically determining that the patient has CKD or does not have CKD based on the medical data in the electronic record.

Implementations of this aspect may include one or more of the following features:

In some implementations, the step of automatically determining that the patient has CKD includes determining whether the patient has diabetic CKD, has diabetic/hypertensive CKD, has hypertensive CKD, or does not have CKD. In some implementations, the step of automatically determining that the patient has diabetic CKD, has diabetic/hypertensive CKD, has hypertensive CKD, or does not have CKD is further based on one or more exclusion criterion.

Implementations of the above aspects may include one or more of the following benefits:

Some implementations can be used to provide improved medical diagnoses of current and future patients, provide more accurate predictions of patient outcome, and improve the overall quality of clinical care. In some implementations, a diagnosis can be automatically rendered using electronic medical records, freeing up a clinician to treat other patients instead of reviewing voluminous medical histories. As a result, implementations of the above aspects can save time and money for both patients and clinicians, and render more accurate and reliable diagnoses.

DETAILED DESCRIPTION

As noted above, electronic medical records (EMRs) can provide large amounts of information regarding large numbers of patients. For example, EMRs can contain collections of longitudinal phenotypic data that potentially offers valuable information for discovering clinical population subtypes, and can potentially be used in association studies in medical research and in the prediction of outcomes in patient care. In many cases, information contained in EMRs can be used to provide improved medical diagnoses of current and future patients, provide more accurate predictions of patient outcome, and improve the overall quality of clinical care.

When matched to information contained in biobanks (e.g., information and/or biological samples), EMRs can be used to identify traits/phenotypes in a large number of patients for biomarker/genomics research, thereby substantially reducing the effort and time needed to identify markers or variants that influence disease development, progression, or medication response. Also, as data are available in a longitudinal form, the disease progression can be analyzed using advanced statistical methodology and differential rates of progression defined to identify patients at highest risk of progression.

For the above purposes, accurate and high throughput phenotyping is often necessary. Though manual review of the EMR for phenotyping is considered to be the "ground truth", in reality, it is effort-intensive, time-consuming, and expensive, with variable accuracy and precision depending on the abstractor. Though ICD-9 codes have been used in the past for phenotyping purposes, previous studies for diseases ranging from rheumatoid arthritis to cardiovascular disease have demonstrated that sole use of these codes is not sufficient. Also, data solely from patient history is often considered to be insufficient.

To overcome these problems, data from disparate sources such as diagnosis and procedure codes, laboratory data, medication use, and imaging studies can be mined from the EMR and processed using various techniques in order to identify cases and controls with a high degree of accuracy and confidence.

Here, we describe various implementations for automatically making medical diagnoses using phenotypic analysis.

In an illustrative example case, we describe the development and validation of an automated technique that combines data from various sources to identify diabetic and hypertensive CKD (DHCKD), diabetic CKD (DCKD), and hypertensive CKD (HCKD) cases of stage 3 or higher. We also tested the hypothesis that use of this integrated approach to identify CKD may be more accurate and reliable than use of ICD-9 codes alone.

Figure 1:
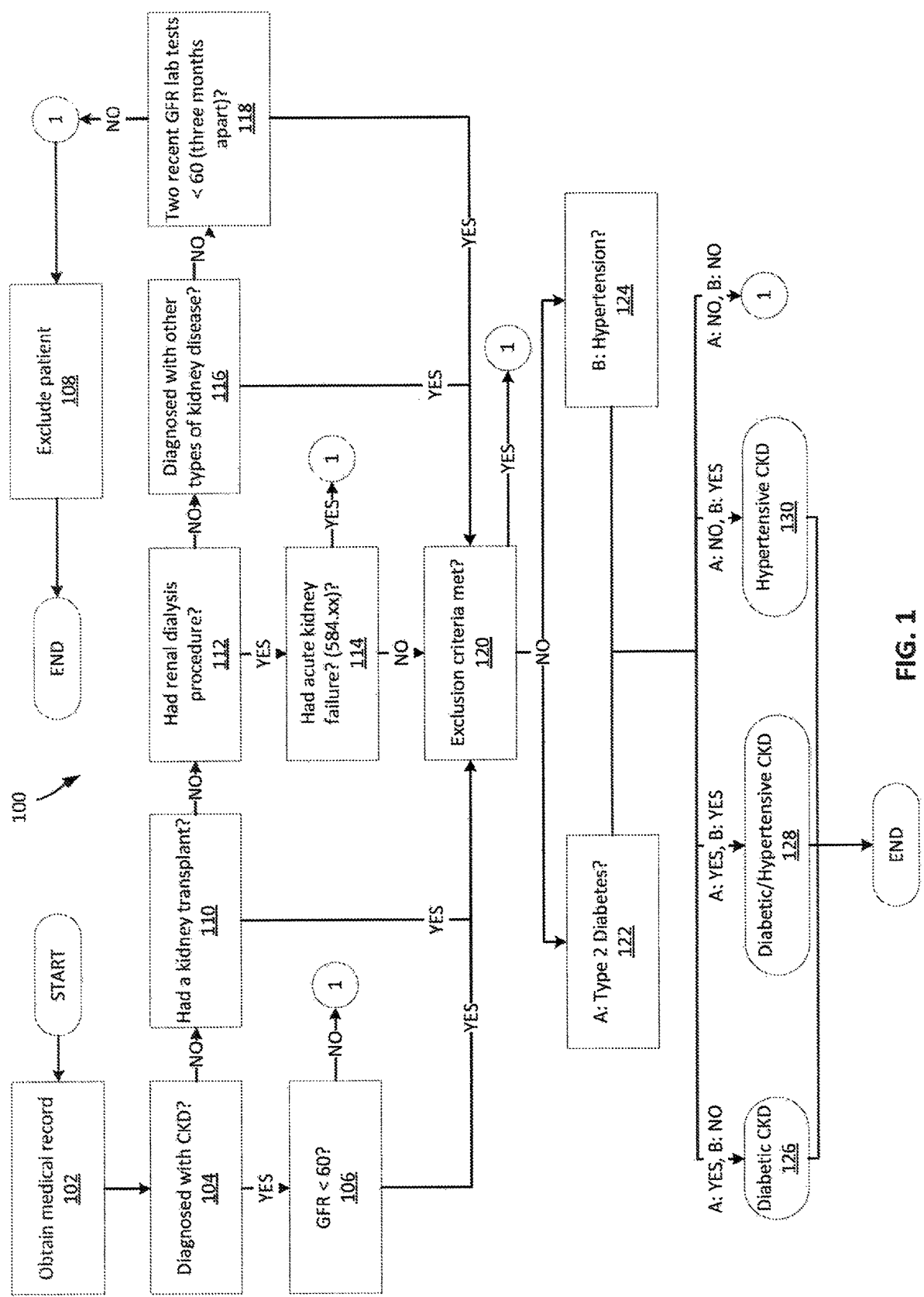
FIG. 1 is a diagram of an example process for making an automated medical diagnosis.

An example phenotyping process 100 for automatically identifying patients with diabetic/hypertensive CKD is shown in FIG. 1. In example applications, the process 100 provides a comprehensive approach for incorporating ICD-9 codes, relevant medications, and pertinent laboratory test results to identify CKD cases of stage 3 or higher.

The process 100 begins by obtaining medical records for a patient (step 102). In some implementations, a record can include information regarding the patient's medical history. For example, a record can indicate whether the patient has been diagnosed with particular diseases or conditions (e.g., CKD, other types of kidney diseases, type 2 diabetes, hypertension, and so forth). A record can also indicate various medical events in the patient's past (e.g., a history of treatments or procedures that the patient has undergone). For example, a record can indicate if the patient had previously undergone a kidney transplant, if the patient had previously undergone a renal dialysis procedure, and so forth. A record can also include information regarding laboratory tests or other medical assays that have been performed in the past. As examples, a record can indicate a patient's systolic blood pressure (SBP), low-density lipoproteins (LDL), high-density lipoproteins (HDL), triglycerides, hemoglobin A1C, or estimated glomerular filtration rate (eGFR), among other biological metrics. A record can also indicate demographic information or other information pertaining to the patient (e.g., location, age, gender, ethnicity, and so forth). As other examples, a measurement value can indicate the answer to a question (e.g., an indication if a patient meets a particular criterion, for example if the patient has been previously diagnosed with a particular disease). In some implementations, a measurement value can be a value in a continuous range, a binary value (e.g., true/false, yes/no, or an indication of gender), or value from a discrete set of possible values (e.g., an indication of a particular category, or a particular integer score or metric determined using a scoring rubric). In some implementations, each measurement value can also include information regarding when that measurement value was observed. As an example, a data set could include several measurement values, where each measurement value is associated with a respective time point.

In some cases, the records can be obtained from electronic medical records (EMRs). As an example, medical information regarding a patient can be stored, maintained, and retrieved from one or more computer systems (e.g., client computers, server computers, distributed computing systems, and so forth) or other devices capable of retaining electronic data. In an example implementation, medical information regarding a patient can be transcribed into an EMR, transmitted to a computer system for storage, revised over time (e.g., to add, delete, or edit data), and retrieved for review. In some implementations, multiple EMR can be stored in this manner in the form of a database. As an example, multiple EMRs, each referring to a different patient, can be transmitted to a computer system for storage, then individually revised or retrieved for review at a later point in time.

After a patient's records are obtained, a determination is made whether the patient has been previously diagnosed with CKD (step 104). This determination can be made in various ways. For example, in some cases, the determination can be made based on a particular flag or data value in the patient's record, indicating that he has been previously diagnosed with CKD.

If it is determined that the patient has been previously diagnosed with CKD, it is determined if the patient has had a GFR test with a result less than 60 (step 106). This determination can be made in various ways. For example, in some cases the determination can be made based on data in the patient's record describing previously conducted examinations (e.g., laboratory test results).

If it is determined that the patient has had a GFR test with a result greater than 60, the patient is excluded, and no diagnosis rendered (step 108).

Referring back to step 104, if it is determined that the patient has not been previously diagnosed with CKD, it is determined if the patient has previously undergone a kidney transplant (step 110). As with step 104, this determination can be made in various ways. For example, in some cases, the determination can be made based on a particular flag or data value in the patient's record, indicating that he has previously undergone a kidney transplant.

If it is determined that the patient has not previously undergone a kidney transplant, it is determined if the patient has previously undergone a renal dialysis procedure (step 112). As with steps 104 and 110, this determination can be made in various ways. For example, in some cases, the determination can be made based on a particular flag or data value in the patient's record, indicating that he has previously undergone a renal dialysis procedure.

If it is determined that the patient has previously undergone a kidney transplant, it is determined if the patient has previously had acute kidney failure (step 114). As with steps 104, 110, and 112, this determination can be made in various ways. For example, in some cases, the determination can be made based on a particular flag or data value in the patient's record, indicating that he has previously had acute kidney failure. In some implementations, acute kidney failure can be indicated by a particular International Statistical Classification code stored within the patient's records. For example, an acute kidney failure can be indicated by an ICD-9 code of 584.xx.

If it is determined that the patient has had acute kidney failure, the patient is excluded, and no diagnosis rendered (step 108).

Referring back to step 112, if it is determined that the patient has not previously had acute kidney failure, it is determined if the patient has previously been diagnosed with another type of kidney disease (step 116). As with steps 104, 110, 112, and 114, this determination can be made in various ways. For example, in some cases, the determination can be made based on a particular flag or data value in the patient's record, indicating that he has previously had acute kidney failure.

If it is determined that the patient has not previously been diagnosed with another type of kidney disease, it is determined if the patient has had two GFR tests with a result less than 60, where the two GFR tests are at least three months apart (step 118). As with step 106, this determination can be made in various ways. For example, in some cases the determination can be made based on data in the patient's record describing previously conducted examinations (e.g., laboratory test results).

If it is determined that the patient has not had two GFR test with a result less than 60, where the two GFR tests are at least three months apart, the patient is excluded, and no diagnosis is rendered (step 108).

Referring back to steps 106, 110, 114, 116, and 118, a) if it is determined that the patient has had a GFR test with a result less than 60 (with respect to step 106), b) if it is determined that the patient has previously undergone a kidney transplant (with respect to step 110), c) if it is determined that the patient has not previously had acute kidney failure (with respect to step 114), d) if it is determined that the patient has previously been diagnosed with another type of kidney disease (with respective step 116), or e) if it is determined that the patient has had two GFR tests with a result less than 60, where the two GFR tests are at least three months apart (with respect to step 118), then it is determined if particular exclusion criteria are met (step 120). Exclusion criteria can vary, depending on the implementation. For example, in some implementations, a patient can be excluded if his record is designated as confidential; this designation can be, for example, stored as a flag or data value in the patient's records. In some implementations, a patient can be excluded if the patient is a pediatric patient; the patient's age and status can be determined, for example, using flags or data values in the patient's records. In some implementations, a patient can be excluded if the patient does not have particular laboratory test results in the system, or if the patient does not have any laboratory test results at all; this can be determined, for example, by ascertaining if a patient's records contain certain laboratory test results of interest. For example, in some cases, a patient might be excluded if his records do not contain any laboratory test results. As another example, in some cases, a patient might be excluded if his records do not contain any laboratory test results with GFR measurements. Although example exclusion criteria are described above, these are merely examples. In practice, other exclusion criteria can also be used. Further, a single exclusion criterion or multiple exclusion criteria can be used, depending on the implementation.

If it is determined that the exclusion criteria are met, the patient is excluded, and no diagnosis is rendered (step 108).

If it is determined that the exclusion criteria re not met, it is determined if the patient has type 2 diabetes (step 122) and if the patient has hypertension (step 124). Steps 122 and 124 can be performed concurrently (e.g., at the same time or approximately the same time) or sequentially (e.g., one after the other). As with steps 104, 110, 112, 114, and 116, this determination can be made in various ways. For example, in some cases, the determination can be made based on particular flags or data values in the patient's record, indicating that he has type 2 diabetes or hypertension. If it is determined that the patient has type 2 diabetes but does not have hypertension, a diagnosis of diabetic CKD is rendered for the patient (step 126). If it is determined that the patient has both type 2 diabetes and hypertension, a diagnosis of diabetic/hypertensive CKD is rendered for the patient (step 128). If it is determined that the patient does not have type 2 diabetes but does have hypertension, a diagnosis of hypertensive CKD is rendered for the patient (step 130). If it is determined that the patient has neither type 2 diabetes nor hypertension, the patient is excluded, and no diagnosis is rendered (step 108).

In this manner, the process 100 uses a series of criteria to determine if the patient has diabetic CKD and/or hypertensive CKD, or if the patient can be excluded. Process 100 can be used, for example, to identify patients who have diabetic CKD and/or hypertensive CKD (or are suspected of having diabetic CKD and/or hypertensive CKD) based solely or substantially on their medical records. After these patients are identified, clinician can then provide the appropriate medical care. In some implementations, process 100 can supplement other diagnostic techniques. For example, the process 100 can be used to validate, support, or challenge diagnoses made using other diagnostic techniques, or to otherwise provide additional information in order to make a final diagnosis.

In some implementations, a computer system can perform process 100 with respect to a single patient or with respect to multiple patients in order to automatically identify in one or more patients of interest having (or suspected of having) diabetic CKD and/or hypertensive CKD. In some implementations, the computer system can perform process 100 continuously in order to identify patients of interest on a continuous basis. For example, during the course of clinical care, one or more clinicians might update a database of patient data (e.g., a database of EMRs) based on the results of the care. A computer system can continuously perform process 100 in order to find patients of interest as soon as a particular diagnosis can be rendered. In some implementations, the computer system can perform process 100 on demand (e.g., based on a command provided by a clinician or technician) in order to identify patients of interest at a user-designed time. In some implementations, the computer system can perform process 100 on a particular patient record when the patient record is revised (e.g., when it is updated with new information). In this manner, the computer system can monitor each of the data records and perform process 100 only when a possible change in diagnosis might occur. Although several example implementations are described, these are merely examples. In practice, process 100 can be performed using other systems or groups of systems, depending on the application. Likewise, process 100 can be performed continuously, on demand, and/or based on other criteria, depending on the application.

Figure 2:
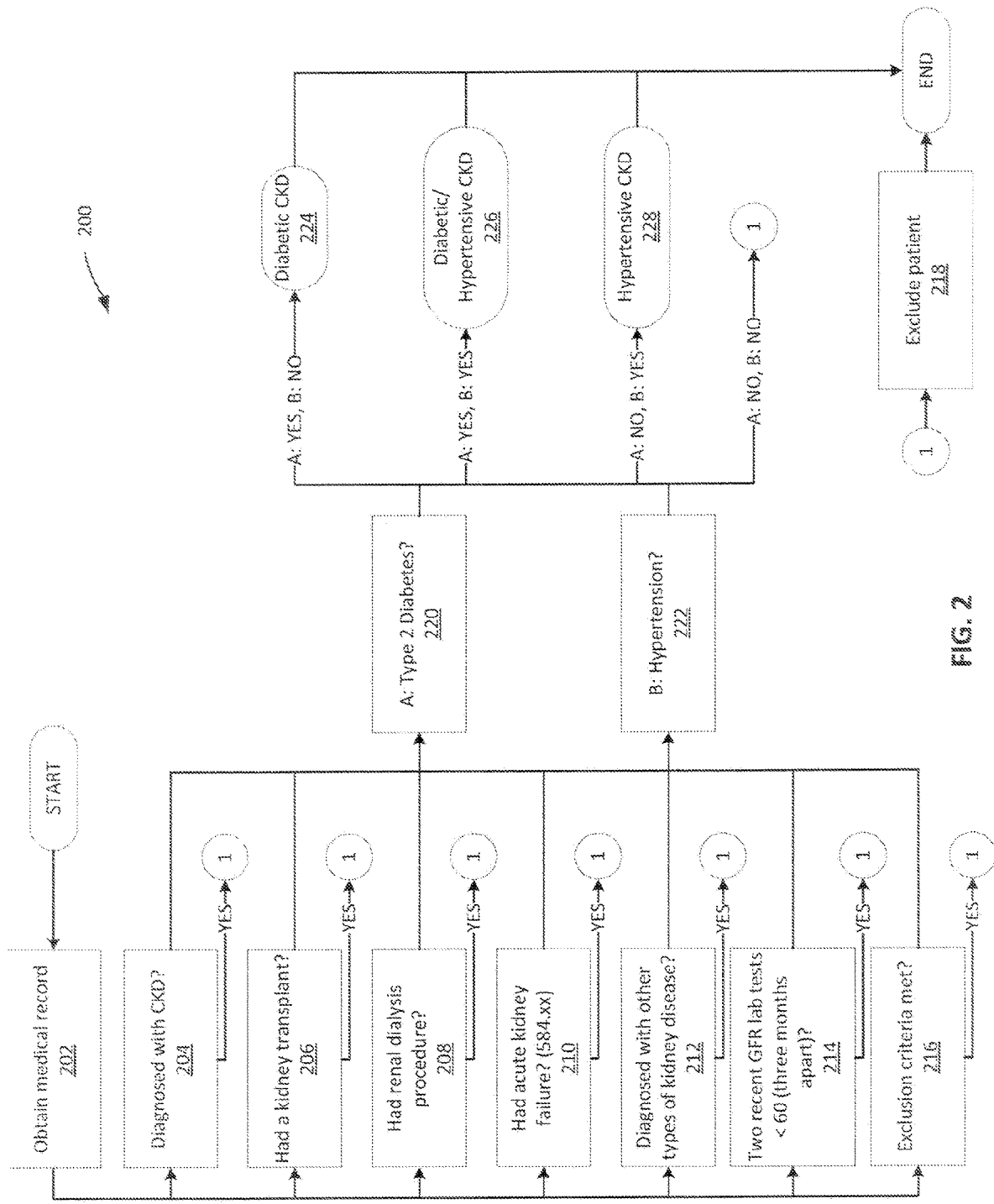
FIG. 2 is a diagram of an example control process.

As a comparison, the results of process 100 can be evaluated against the results from a control process 200. An example control process 200 is shown in FIG. 2. The process 200 begins by obtaining medical records for a patient (step 202). Step 202 can be similar to step 102, as described above.

After a patient's records are obtained, determinations are made whether the patient has been previously diagnosed with CKD (step 204), whether the patient has previously undergone a kidney transplant (step 206), whether the patient has previously undergone a renal dialysis procedure (step 208), whether the patient has previously had acute kidney failure (step 210), whether the patient has previously been diagnosed with another type of kidney disease (step 212), whether the patient has had two GFR tests with a result less than 60, where the two GFR tests are at least three months apart (step 214), and whether particular exclusion criteria are met (step 216). Steps 204, 206, 208, 210, 212, 214, and 216 can be similar to the corresponding steps in process 100, as described above. For example, steps 204, 206, 208, 210, 212, 214, and 216 can be similar to steps 104, 110, 112, 114, 116, and 118, respectively.

If any of steps 204, 206, 208, 210, 212, 214, and 216 results in a positive determination (e.g., "yes"), then the patient is excluded, and no diagnosis is rendered (step 218). Step 218 can be similar to step 108, as described above. For example, a patient can be excluded if it is determined that the patient has been previously diagnosed with CKD, if the patient has previously undergone a kidney transplant, if the patient has previously undergone a renal dialysis procedure, if the patient has previously had acute kidney failure, if the patient has previously been diagnosed with another type of kidney disease, if the patient has had two GFR tests with a result less than 60, where the two GFR tests are at least three months apart (step 214), and/or if particular exclusion criteria are met (step 216).

If none of steps 204, 206, 208, 210, 212, 214, and 216 are determined to be true, it is determined if the patient has type 2 diabetes (step 220) and if the patient has hypertension (step 222). Steps 220 and 222 can be similar to steps 122 and 124, as described above. If it is determined that the patient has type 2 diabetes but does not have hypertension, a diagnosis of diabetic CKD is rendered for the patient (step 224). If it is determined that the patient has both type 2 diabetes and hypertension, a diagnosis of diabetic/hypertensive CKD is rendered for the patient (step 226). If it is determined that the patient does not have type 2 diabetes but does have hypertension, a diagnosis of hypertensive CKD is rendered for the patient (step 228). If it is determined that the patient has neither type 2 diabetes nor hypertension, the patient is excluded, and no diagnosis is rendered (step 218).

As described above, implementations of the above described techniques can be used to diagnose patients with respect to CKD based on patients' medical records. An example application is described below.

In this example, we randomly selected 200 cases and 200 controls for diabetic chronic kidney disease (DCKD), hypertensive chronic kidney disease (HCKD) and diabetic/hypertensive chronic kidney disease (DKCHK) using implementations of the process 100 and 200, respectively, from the an example database of EMRs. Two independent physician reviewers manually reviewed each medical record. In this case, the "gold standard" (e.g., a comparative diagnostic test or benchmark) for a case or a control was considered to be manual review by the physician reviewers. Any differences in agreement were arbitrated after discussion between the two reviewers.

We also ascertained whether chronic kidney disease was identified in the EMR using ICD-9 codes. The codes used for this purpose were the CKD hierarchy of codes, as shown in Table 1. We considered a control as correctly identified by ICD-9 codes if there was a diagnostic code identifying hypertension and/or diabetes as shown without an accompanying Table 1. While reviewing the charts, we also abstracted urine protein measurement as microalbumin/creatinine ratio and/or urine protein/creatinine ratio. When multiple measurements were available, we recorded the most recent measurement. We also abstracted whether the patient had been referred to a nephrologist.

TABLE 1

ICD-9 codes used for identifying cases and controls.

| Disease | ICD-9 code |
|---|---|
| End stage renal disease | 585.1 to 585.9 |
| Hypertensive chronic kidney disease, unspecified, with chronic kidney disease stage I through stage IV, or unspecified | 403.90 |
| Hypertensive nephropathy | 403.10 |
| Hypertensive renal disease | 403 |
| Hypertensive heart and renal disease | 404 |
| Diabetic nephropathy | 583.81 |
| Diabetic nephrosis | 581.81 |
| Diabetes with renal manifestations, type II or unspecified type, not stated as uncontrolled | 250.40 |
| Diabetes with renal manifestations, type II or unspecified type, uncontrolled | 250.42 |
| Diabetes with other specified manifestations, type II or unspecified type, not stated as uncontrolled | 250.80 |

TABLE 1-continued

ICD-9 codes used for identifying cases and controls.

| Disease | ICD-9 code |
|---|---|
| Diabetes with other specified manifestations, type II or unspecified type, uncontrolled | 250.82 |
| Intercapillary glomerulosclerosis | 581.81 |
| Kimmelstiel-Wilson syndrome | 581.81 |
| Hypertension | 401-405 excluding 403 and 404 |
| Diabetes | 250.00 to 250.93 excluding 250.40, 250.42, 250.80 and 250.82) |

After manually reviewing the cases, we calculated the inter-rater agreement/kappa statistic between the two physician reviewers. We then calculated summary statistics for both the phenotyping CKD process 100 and ICD-9 codes with manually reviewed cases and controls as the gold standard. The primary outcome statistics of interest were positive and negative predictive values along with the positive and negative likelihood ratios. We also calculated receiver-operating curves (ROC) to calculate the area under the curve for both the phenotyping CKD process 100 and the ICD-9 codes with the gold standard again being manual review of charts. We also calculated summary statistics (including missing values) for the urine protein measurements and the proportion of patients that had been referred to a nephrologist. We performed these analyses separately for each category of CKD.

Figure 3:
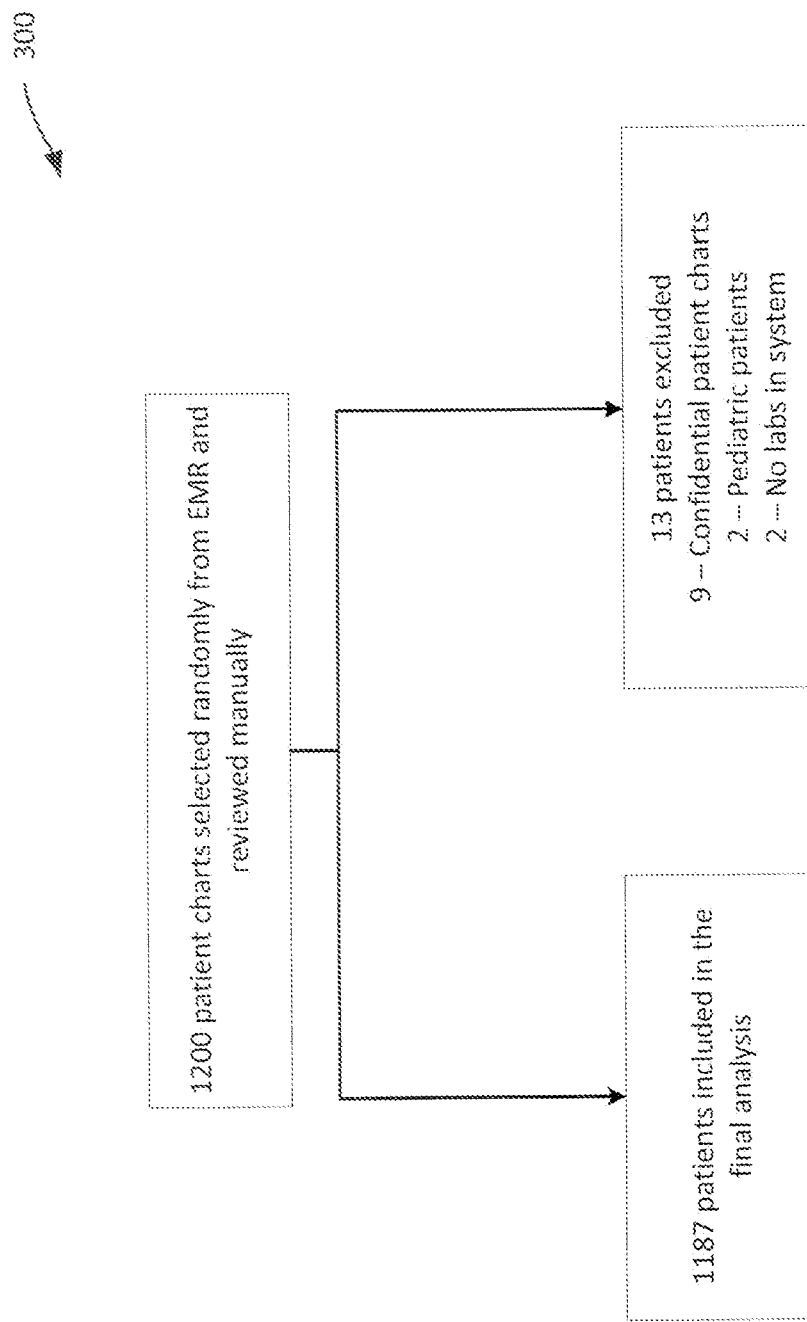
FIG. 3 is a diagram of an example selection of patient records.

We reviewed 1200 medical records. These were divided into 3 case case/control groups with 200 records each of DCKD, HCKD and DHCKD cases and 200 each of DCKD, HCKD and DHCKD controls. Out of these 1200 patients, 13 (1.1%) were excluded due to confidential status or missing data, leaving 1187 patients included in the final analysis. FIG. 3 shows a chart 300 for the final selection of patient records, as described above. As shown in FIG. 3, nine patients were excluded as having confidential patient charts, two patients were excluded for being pediatric patients, and two were excluded because they did not have any laboratory test results in the system.

We calculated the inter-rater agreement/kappa statistic between the two independent reviewers. There was good inter-rater agreement at 90% that did not vary significantly between the categories (89% for DCKD; 91.3% for HCKD and 89% for DHCKD). After arbitration of disagreements and excluding 14 cases, there were a total of 599 cases (202 for DCKD, 197 for HCKD and 200 for DHCKD) and 587 controls (190 for DCKD, 200 for HCKD and 197 for DHCKD) by manual review which were considered the gold standard for both cases and controls.

For analysis of DCKD, we included 393 patients. Table 2a shows the percent of cases identified by the phenotyping CKD process 100 and ICD-9 codes. With regards to diabetes, the phenotyping CKD process 100 correctly identified 187/202(92.6%) cases and 181/190(95.3%) of controls. In contrast, the ICD-9 codes correctly identified only 90/202 (44.6%) cases and 151(79.5%) of controls. Table 1a shows the sensitivity and specificity of each method. Again, the phenotyping CKD process 100 significantly outperformed ICD-9 codes with a positive predictive value of 95.4%, a negative predictive value of 92.3%, a positive likelihood ratio of 19.5 and a negative likelihood ratio of 0.08.

TABLE 2a

Comparison of phenotyping CKD process to ICD-9 codes for diabetic CKD using manual review of medical records as a gold standard

|  | CKD Process | | ICD-9 codes | |
|---|---|---|---|---|
| Manual review of charts | Controls | Cases | Controls | Cases |
| Controls | 181 | 9 | 151 | 39 |
| Cases | 15 | 187 | 112 | 90 |

|  | Estimate in % | 95% Confidence Interval | Estimate in % | 95% Confidence Interval |
|---|---|---|---|---|
| Positive Predictive Value | 95.4 | 81.2 to 97.7 | 69 | 60 to 79.8 |
| Negative Predictive Value | 92.3 | 87.4 to 95.5 | 57 | 51 to 63 |
| Positive Likelihood Ratio | 19.5 | 10.3 to 37 | 2.17 | 1.58 to 2.99 |
| Negative Likelihood Ratio | 0.08 | 0.05 to 0.13 | 0.70 | 0.61 to 0.79 |

Figure 4A:
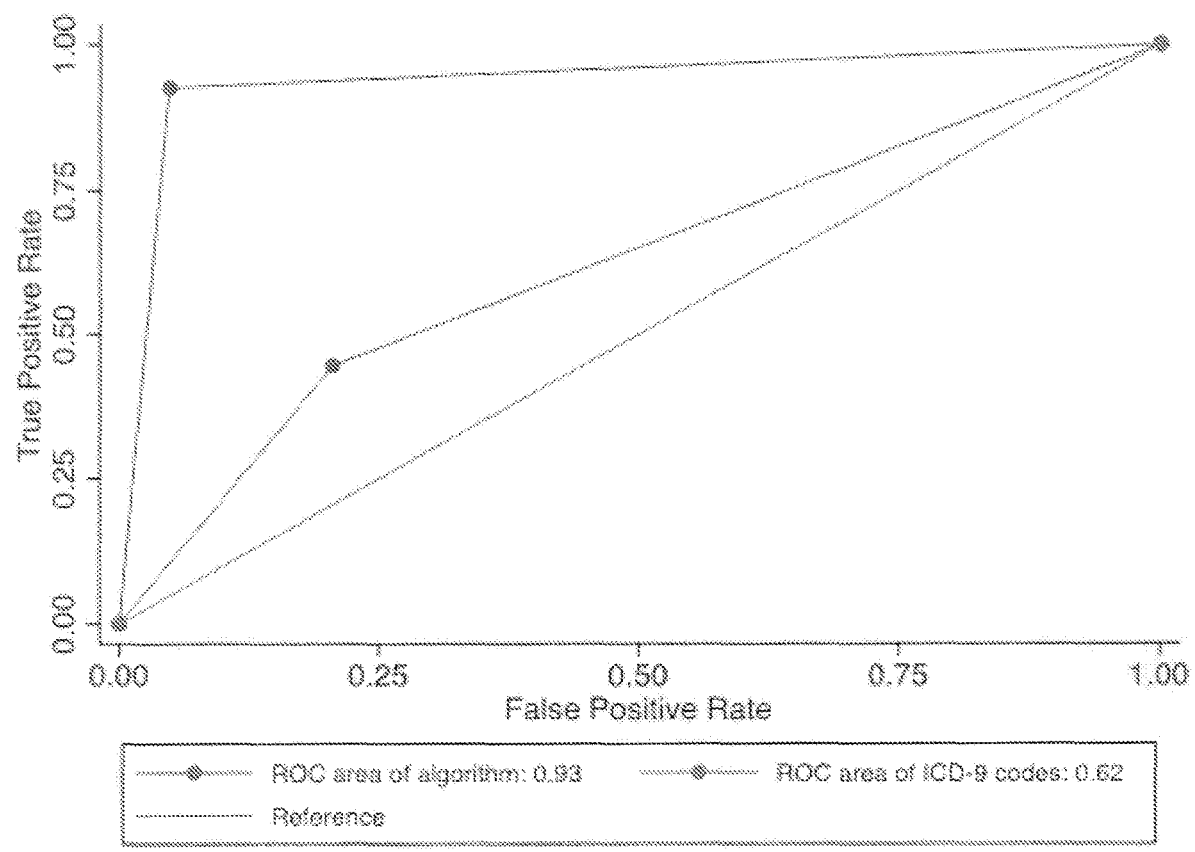
FIG. 4A is a chart showing ROC curves comparing the phenotyping CKD process and the ICD-9 codes to identify diabetic CKD cases and controls.

We also calculated the ROC for the phenotyping CKD process 100 vs. ICD-9 codes with the manual review as gold standard. Again, the phenotyping CKD process 100 significantly outperformed the ICD-9 codes with an AUC of 0.94(95% Confidence Interval 0.92 to 0.96) vs. the ICD-9 codes (AUC of 0.62 with 95% Confidence Interval 0.58 to 0.66) (as shown in FIG. 4A).

Figure 4B:
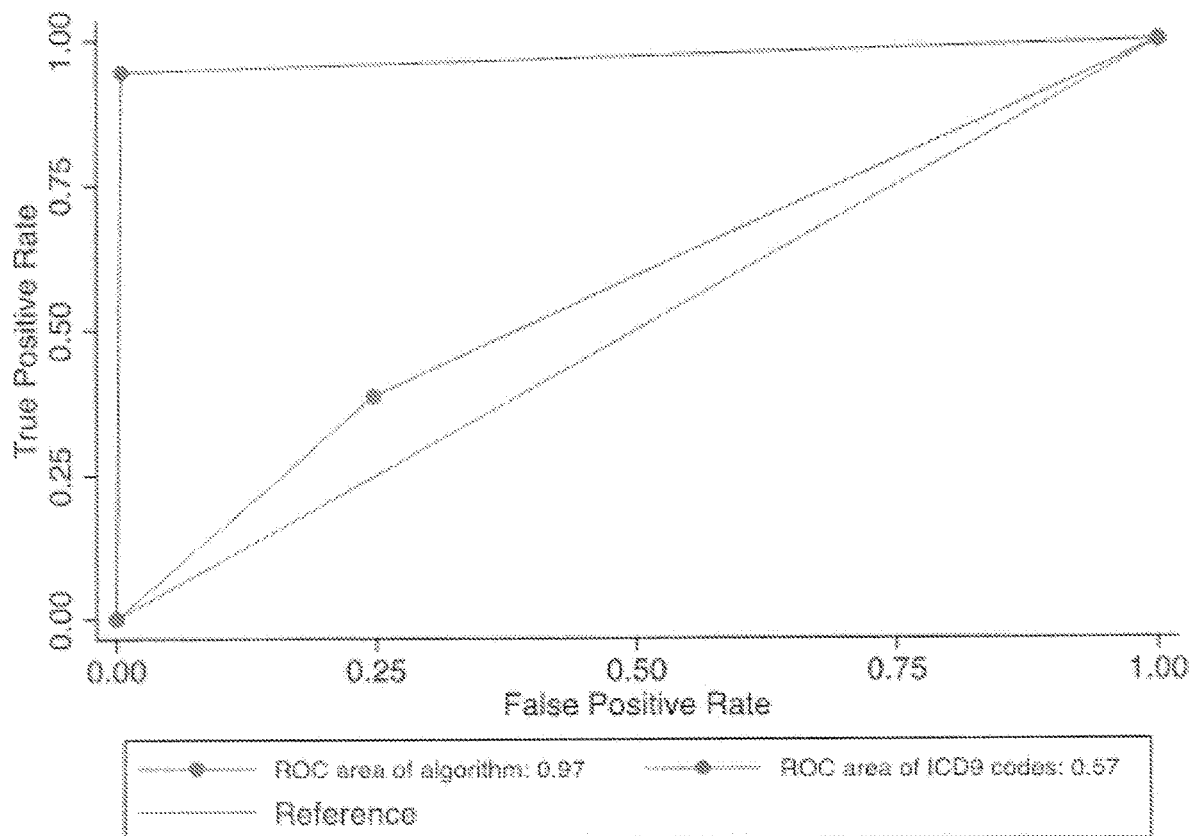
FIG. 4B is a chart showing ROC curves comparing the phenotyping CKD process and the ICD-9 codes to identify hypertensive CKD cases and controls

With regards to HCKD, 397 patients were included. Table 2b shows the performance of both the phenotyping CKD process 100 and the ICD-9 codes. The phenotyping CKD process 100 correctly identified 196/197(99%) cases and 189/200(94.7%) controls. Table 2b shows the sensitivity and specificity of each technique. The phenotyping CKD process 100 significantly outperformed ICD-9 codes with a positive predictive value of 99%, a negative predictive value of 94.7%, a positive likelihood ratio of 180 and a negative likelihood ratio of 0.05. After ROC analysis, the AUC of the phenotyping CKD process 100 was 0.97(95% Confidence Interval 0.95 to 0.99) compared to an AUC of 0.57 for ICD-9 codes (95% Confidence Interval 0.52 to 0.61) (as shown in FIG. 4B).

TABLE 2b

Comparison of CKD process to ICD-9 codes for hypertensive CKD using manual review of medical records as a gold standard

|  | CKD Process | | ICD-9 codes | |
|---|---|---|---|---|
| Manual review of charts | Controls | Cases | Controls | Cases |
| Controls | 189 | 1 | 143 | 47 |
| Cases | 11 | 196 | 127 | 80 |

|  | Estimate in % | 95% Confidence Interval | Estimate in % | 95% Confidence Interval |
|---|---|---|---|---|
| Positive Predictive Value | 99 | 96.6 to 99.9 | 63 | 53.9 to 71.2 |
| Negative Predictive Value | 94.7 | 90.4 to 97.2 | 52.9 | 46.8 to 59 |
| Positive Likelihood Ratio | 180 | 25.5 to 1271 | 1.56 | 1.16 to 2.11 |
| Negative Likelihood Ratio | 0.05 | 0.03 to 0.09 | 0.89 | 0.78 to 1.01 |

Figure 4C:
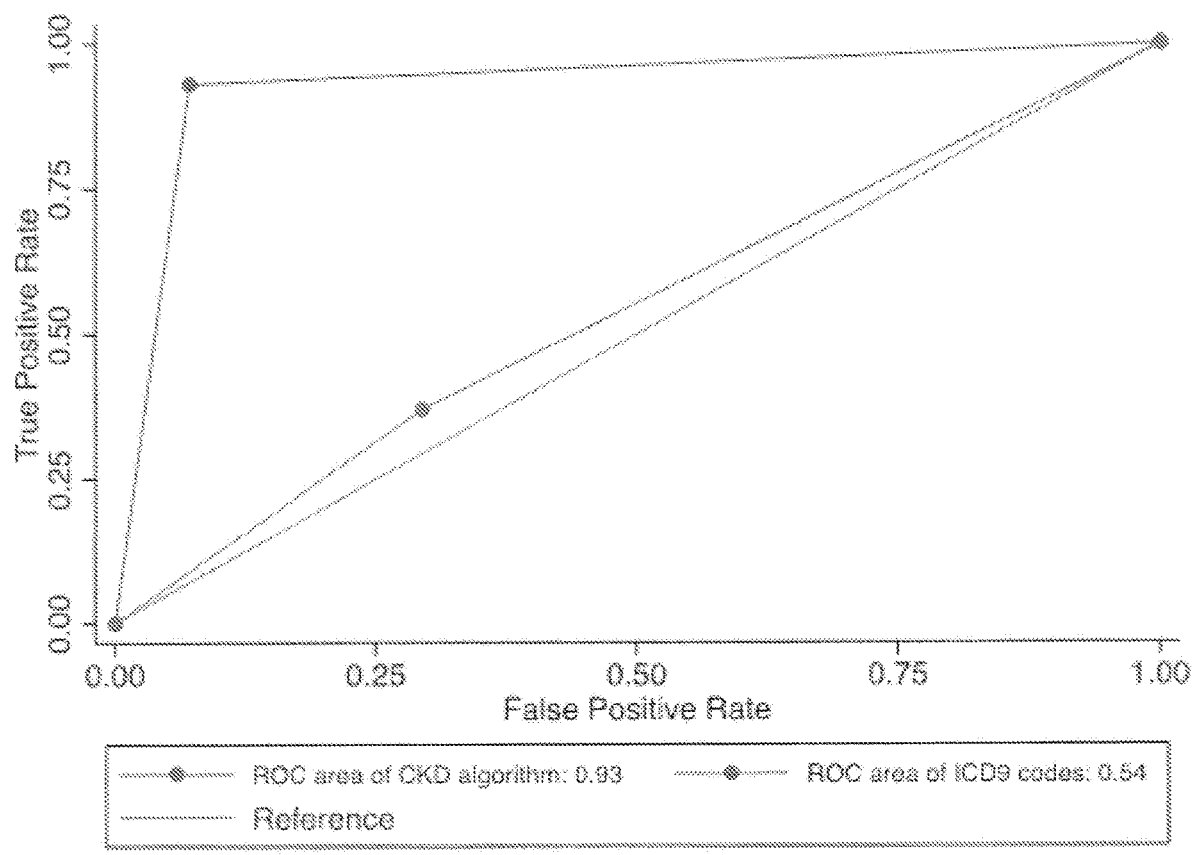
FIG. 4C is a chart showing ROC curves comparing the phenotyping CKD process and the ICD-9 codes to identify diabetic and hypertensive CKD cases and controls.

We included 397 patients in the final analysis for DHCKD. The phenotyping CKD process 100 correctly identified 186/200(93%) of cases and 183/197(92.8%) of controls. It had a negative predictive value of 92.8%, a positive likelihood ratio of 13.1 and a negative likelihood ratio of 0.08. The comparison between the phenotyping CKD process 100 and ICD-9 codes is presented in Table 2c. Again on ROC analysis, the AUC was significantly higher for the phenotyping CKD process 100 (0.93; 95% Confidence Interval 0.90 to 0.95) as compared to the ICD-9 codes (0.54; 95% Confidence Interval 0.49 to 0.58) (as shown in FIG. 4C).

TABLE 2c

Comparison of phenotyping CKD process to ICD-9 codes for diabetic and hypertensive CKD using manual review of medical records as a gold standard

|  | CKD Process | | ICD-9 codes | |
|---|---|---|---|---|
| Manual review of charts | Controls | Cases | Controls | Cases |
| Controls | 183 | 14 | 139 | 58 |
| Cases | 14 | 186 | 126 | 74 |

|  | Estimate in % | 95% Confidence Interval | Estimate in % | 95% Confidence Interval |
|---|---|---|---|---|
| Positive Predictive Value | 93 | 88.3 to 95.9 | 56 | 47 to 65 |
| Negative Predictive Value | 92.8 | 88 to 95.9 | 52 | 46 to 59 |
| Positive Likelihood Ratio | 13.1 | 7.9 to 21.7 | 1.26 | 0.95 to 1.66 |
| Negative Likelihood Ratio | 0.08 | 0.05 to 0.12 | 0.89 | 0.80 to 1.00 |

In a secondary analysis we also calculated the urine protein/creatinine or the urine microalbumin/creatinine values for the three categories. These results are shown in Table 3. For DCKD, the median microalbumin/creatinine ratio was 39 and 30% of patients did not have a measurement. Similarly for HCKD the median microalbumin/creatinine ratio was 5.5 and the protein/creatinine ratio was 30 with 98% and 87% patients without a measurement. For DHCKD, the median microalbumin/creatinine and protein/creatinine ratios were 35 and 15, with 37% and 61% of patients respectively lacking measurements at any point of time.

TABLE 3

Microalbuminuria and proteinuria measurement in CKD cases and controls

|  | Median (IQR) | N (%) of missing values |
|---|---|---|
| Diabetic CKD | | |
| Microalbumin/Creatinine | 39 (10-215) | 59/200 (30) |
| Hypertensive CKD | | |
| Urine microalbumin/creatinine | 5.5 (3-28) | 196/200 (98) |
| Urine protein/creatinine in mg/gm | 30 (30-300) | 173/200 (87) |
| Diabetic and hypertensive CKD | | |
| Urine microalbumin/creatinine | 35 (8-127) | 74 (37) |
| Urine protein/creatinine in mg/gm | 15 (6.5-64) | 122 (61) |

We also ascertained the proportion of participants that were referred to a nephrologist during any point of their clinical course in the EMR. Out of a total of 599 cases, only 112(18.7%) were referred to a nephrologist at any point during their course.

Implementations of this process can provide various benefits. For example, it is anticipated that EMRs will become extremely important sources of data for both clinical and genomic association studies. Since data are present in a longitudinal form, it may facilitate studying the natural history of a disease process as well as the response to treatment in the "real world" scenario. However, the identification of particular phenotypes, especially chronic, complex diseases, is challenging because of the complexity of the data itself and the way in which it is recorded in the EMR. However, with government interest driving the widespread use and adoption of EMRs, this provides a vast and as-yet relatively untapped resource. If robust phenotypes can be constructed using meaningful information from various sources in the EMR, it would provide significant value for identifying patient cohorts that satisfy complex criteria.

A recent review discussed the approaches aimed at automatically identifying patients with a common phenotype. Machine learning approaches using electronic phenotyping and statistical analyses are more popular in recent years as compared to simpler rule based systems. The utility of such phenotyping techniques is manifold, including discovering novel genetic associations of complex diseases, tracking their natural history, isolating patients for clinical trials, and ensuring quality control in large institutions by ensuring that standard of care guidelines are met in these patients.

Chronic kidney disease is one of the most complex and common diseases today. Though there are novel genetic associations including UMOD, APOL1 and SHROOM3, there are other potential genetic associations that explain the differential rates of CKD in different ethnic populations. Clinical decision making is challenging due to variability in the rates of progression and lack of widely-accepted guidelines to identify patients most at risk of progression to ESRD. For studies to assess progression over the course of the patient's history in the EMR, accurate identification of large numbers of patients is needed. To accomplish these goals, researchers need robust phenotyping techniques to effectively leverage disparate data sources in the EMR.

To the best of our knowledge, this process is one of the first automated phenotyping techniques for diabetic/hypertensive CKD. It demonstrates high sensitivity (93-95%) and specificity (93-99%) with manual review as a gold standard. In comparison, the use of ICD-9 codes to identify cases and controls had significantly lower sensitivity (37-44%) and specificity (63-79%). Thus, an integrated approach using diagnostic codes, medications, and laboratory tests yielded significant improvement over non-integrated approaches.

Among this patient cohort, only 20% of patients were referred to a nephrologist at any point during the documented clinical course. Although there are no recommended guidelines for nephrologist referral in CKD stage 3, there are studies suggesting that such referrals may improve prognosis (24,25). Through the identification of cases within an EMR using this process, this low referral rate may be easily increased.

Finally, we abstracted urine microalbumin and protein measurements from the EMR. The median values ranged from 5.5-39 for the microalbumin/creatinine ratio and from 15-30 for the protein/creatinine ratio. Several measurements were missing—30% and 87% in the diabetes and hypertensive group, respectively.

In summary, we describe the development and validation of an automated process for identifying diabetic/hypertensive CKD cases and controls and also demonstrate its superiority over traditional identification using ICD-9 diagnostic codes. Implementations of this process could be used to accurately and rapidly identify a specific target cohort within the EMR for both research and clinical purposes.

Although a case study is shown above with respect to an example database, this is merely an illustrative example. Implementations of the process can also be used to analyze and identify patients from any other suitable database of medical records.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, medical (e.g., EMRs) can be stored, maintained, revised, and/or retrieved using a system implemented using digital electronic circuitry, or in computer software, firmware, or hardware, or in combinations of one or more of them. In another example, processes 100 and 200 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 5:
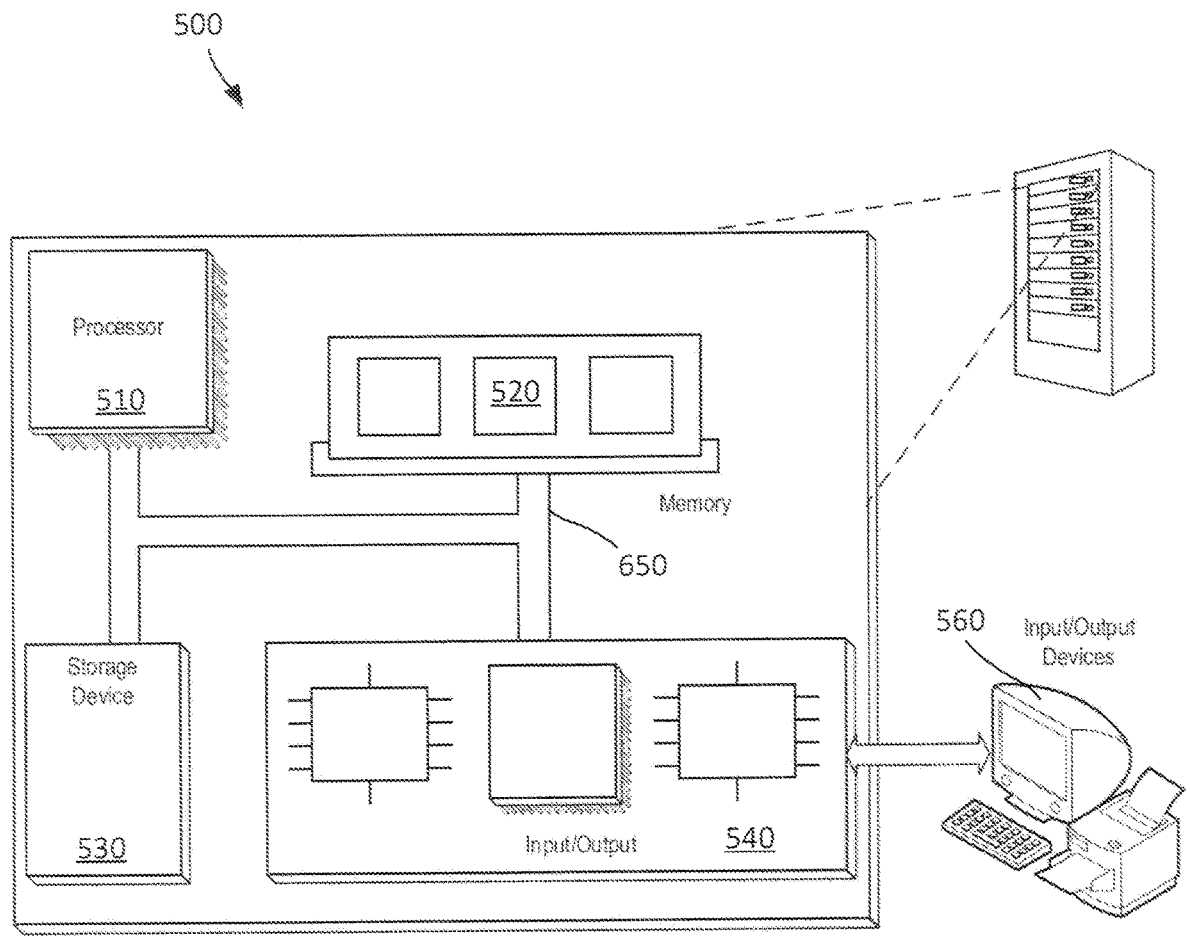
FIG. 5 is a diagram of an example computer system.

FIG. 5 shows an example computer system 500. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. In some implementations, the processor 510 is a single-threaded processor, a multi-threaded processor, or another type of processor. The processor 510 is capable of processing instructions stored in the memory 520 or on the storage device 530. The memory 520 and the storage device 530 can store information within the system 500.

The input/output device 540 provides input/output operations for the system 500. In some implementations, the input/output device 540 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 560. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

Figure 6:
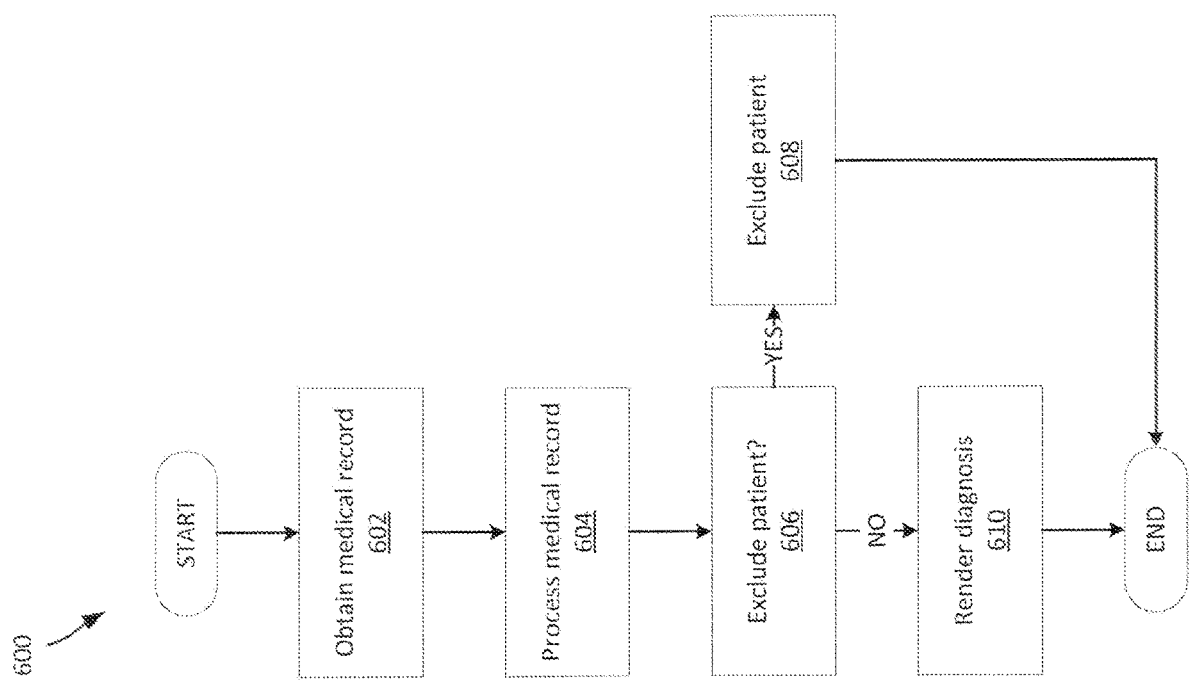
FIG. 6 is a diagram of another example process for making an automated medical diagnosis.

For instance, an example process 600 for automatically identifying patients with diabetic/hypertensive CKD using a computer system 500 is shown in FIG. 6. The process 600 begins by obtaining medical records for a patient (step 602). Step 602 can be similar to step 102, as described above. In an example implementation, the computer system 500 can obtain medical records maintained on the computer system 500 (e.g., within the memory 520 and/or the storage device 530), or in one or more other computer systems communicatively connected to the computer 500 (e.g., a client computer, a server computer, a group of computers, and so forth). For instance, the computer system 500 can electronically request and receive medical records maintained on a server computer through a communications network.

After the patient's records are obtained, the medical record is processed by the computer system 500 (step 604). Processing can include one or more of the steps and the arrangement of steps shown in FIG. 1. For example, processing can include parsing the medical record to determine if the patient has been previously diagnosed with CKD, if the patient has had a GFR test with a result less than 60, if the patient has previously undergone a kidney transplant, if the patient has previously undergone a renal dialysis procedure, if the patient has previously had acute kidney failure, if the patient has previously been diagnosed with another type of kidney disease, if the patient has had two GFR tests with a result less than 60, where the two GFR tests are at least three months apart, if particular exclusion criteria are met, if the patient has type 2 diabetes, and if the patient has hypertension. In an example implementation, the computer system 500 can parse the medical record in search of particular data fields, data flags, or data values that might indicate information that can be used to make these determinations. For instance, the computer system 500 might search for known data fields that contain particular medical examination results (e.g., laboratory test results with GFR measurements), data fields that contain information regarding procedures that have been previously conducted on the patient, data fields that contain information regarding the patient's medical history, and so forth. In some cases, information in the medical record can be arranged in a manner that facilitates processing by computer system 500. For example, various conditions, disease, procedures, and so forth can be represented by alphanumeric or binary codes, such that computer system 500 can readily parse the medical record in search of particular codes. The results of this processing can be stored in the medical record itself (e.g., as a "summary" data field), or it can be stored separate from the medical record (e.g., as a separate file or data object).

After the medical record is processed by the computer system 500, a determination is made whether to exclude the patient (step 606). Determining whether to exclude the patient or not can be performed in a manner similar to that shown in FIG. 1. For example, depending on the combination of results of various determinations made with respect to a patient's medical records, a decision can be made to exclude a patient under certain circumstances, or to not exclude a patient under other circumstances. The computer system 500 can make this determination, for example, by referring to the medical record (e.g., the "summary" data field of the medical record) or to a separate file or data object containing the results of the processing, and using a logic table or decision tree that defines when to exclude a patient and when not to exclude a patient.

If it is determined that the patient should be excluded, then the patient is excluded, and no diagnosis rendered (step 608).

If it is determined that the patient should not be excluded, then the computer system 500 renders a diagnosis (step 610). Determining which diagnosis to render can be performed in a similar manner as shown in FIG. 1. For example, depending on the combination of results of various determinations made with respect to a patient's medical records, a particular diagnosis can be made under certain circumstances, and another diagnosis can be made under other circumstances. The computer system 500 can make this determination, for example, by referring to the medical record (e.g., the "summary" data field of the medical record) or to a separate file or data object containing the results of the processing, and using a logic table or decision tree that defines when render each possible certain diagnosis.

The results of process 600 can be output to a user (e.g., a clinician or technician) though an appropriate output device (e.g., input/output devices 560). The results of process 600 can also be record in the patient's medical record. For example, the computer system 500 can revise the patient's medical record to include the results of process 600, then store the medical record for future retrieval. For example, the computer system 500 can update the patient's medical record, then store the medical record in memory 520 and/or storage device 530, or transmit it to another computer system (e.g., a client computer, a server computer, a group of computers, and so forth) via a communications network for storage.

In some implementations, the computer system 500 can be a dedicated system that solely performs process 600. In some implementations, the computer system 500 can also perform other tasks that are related and/or unrelated to process 600.

A number of implementations have been described. Nevertheless, it will be understood that various modifications may be made without departing from the spirit and scope of the invention. Accordingly, other implementations are within the scope of the following claims.

What is claimed is:

1. A method comprising:
   obtaining, by a computer system, electronic medical records having medical data regarding a plurality of patients, the medical data comprising, for each patient:
   an indication if the patient had been previously diagnosed with CKD,
   an indication if the patient had previously had acute kidney failure,
   an indication if the patient had previously undergone a kidney transplant,
   an indication if the patient had previously undergone a renal dialysis procedure,
   an indication if the patient had previously been diagnosed with another type of kidney disease,
   one or more glomerular filtration rate (GFR) measurements associated with the patient,
   an indication if the patient has type 2 diabetes, and
   an indication if the patient has hypertension;
   automatically identifying, by the computer system, a first subset of patients among the plurality of patients, wherein identifying the first subset of patients comprises identifying, based on the electronic medical records, one or more patients of the plurality of patients that:
   had been previously diagnosed with CKD and are associated with GFR measurements less than a threshold value,
   had previously undergone a kidney transplant,
   had previously undergone a renal dialysis procedure,
   have not had acute kidney failure,
   had previously been diagnosed with another type of kidney disease, and/or
   are associated with two or more GFP measurements less than the threshold value within a threshold period of time,
   automatically identifying, by the computer system, a second subset of patients among the first subset of patients, wherein identifying the second subset of patients comprises identifying, based on the electronic medical records, one or more patients of the first subset of patients that does not satisfy one or more exclusion criteria;
   automatically identifying, by the computer system, a third subset of patients among the second subset of patients, wherein identifying the third subset of patients comprises identifying, based on the electronic medical records, one or more patients of the second subset of patients that:
   have type 2 diabetes, and/or
   have hypertension;
   automatically determining, by the computer system, that the third subset of patients has CKD;
   determining, by the computer system, that a first electronic medical record having medical data regarding a first patient has been modified;
   responsive to determining that the first electronic medical record has been modified:
   making, by the computer system based on the first electronic medical record, a first determination that the first patient:
   had been previously diagnosed with CKD and is associated with GFR measurements less than a threshold value, had previously undergone a kidney transplant,
had previously undergone a renal dialysis procedure,
has not had acute kidney failure,
had previously been diagnosed with another type of kidney disease, and/or
is associated with two or more GFP measurements less than the threshold value within a threshold period of time,
responsive to making the first determination, making, by the computer system based on the first electronic medical record, a second determination that the first patient does not satisfy one or more exclusion criteria, and
responsive to making the second determination, making, by the computer system based on the first electronic medical record, a third determination that the first patient:
has type 2 diabetes, and/or
has hypertension; and
responsive to making the third determination, automatically determining, by the computer system, that the first patient has CKD.

2. The method of claim 1, wherein the step of automatically determining that the third subset of patients has CKD includes determining whether each patient of the third subset of patients has diabetic CKD, has diabetic/hypertensive CKD, or has hypertensive CKD.

3. The method of claim 2, wherein determining whether each patient of the third subset of patients has diabetic CKD, has diabetic/hypertensive CKD, or has hypertensive CKD comprises:
determining that a patient of the third subset of patients has type 2 diabetes and does not have hypertension, and
responsive to determining that the patient of the third subset of patients has type 2 diabetes and does not have hypertension, determining that the patient of the third subset of patients has diabetic CKD.

4. The method of claim 2, wherein determining whether each patient of the third subset of patients has diabetic CKD, has diabetic/hypertensive CKD, or has hypertensive CKD comprises:
determining that a patient of the third subset of patients has type 2 diabetes and has hypertension, and
responsive to determining that the patient of the third subset of patients has type 2 diabetes and has hypertension, determining that the patient of the third subset of patients has diabetic/hypertensive CKD.

5. The method of claim 2, wherein determining whether each patient of the third subset of patients has diabetic CKD, has diabetic/hypertensive CKD, or has hypertensive CKD comprises:
determining that a patient of the third subset of patients does not have type 2 diabetes and has hypertension, and
responsive to determining that the patient of the third subset of patients does not have type 2 diabetes and has hypertension, determining that the patient of the third subset of patients has hypertensive CKD.

6. A method comprising:
creating, by a computer system, electronic medical records having one or more data items regarding a plurality of patients, the one or more data items including, for each patient:
an indication if the patient had been previously diagnosed with CKD,
an indication if the patient had previously had acute kidney failure,
an indication if the patient had previously undergone a kidney transplant,
an indication if the patient had previously undergone a renal dialysis procedure,
an indication if the patient had previously been diagnosed with another type of kidney disease,
one or more glomerular filtration rate (GFR) measurements associated with the patient,
an indication if the patient has type 2 diabetes, and
an indication if the patient has hypertension;
automatically identifying, by the computer system, a first subset of patients among the plurality of patients, wherein identifying the first subset of patients comprises identifying, based on the electronic medical records, one or more patients of the plurality of patients that:
had been previously diagnosed with CKD and are associated with GFR measurements less than a threshold value,
had previously undergone a kidney transplant,
had previously undergone a renal dialysis procedure,
have not had acute kidney failure,
had previously been diagnosed with another type of kidney disease, and/or
are associated with two or more GFP measurements less than the threshold value within a threshold period of time,
automatically identifying, by the computer system, a second subset of patients among the first subset of patients, wherein identifying the second subset of patients comprises identifying, based on the electronic medical records, one or more patients of the first subset of patients that does not satisfy one or more exclusion criteria;
automatically identifying, by the computer system, a third subset of patients among the second subset of patients, wherein identifying the third subset of patients comprises identifying, based on the electronic medical records, one or more patients of the second subset of patients that:
have type 2 diabetes, and/or
have hypertension;
automatically determining, by the computer system, that the third subset of patients has CKD;
determining, by the computer system, that a first electronic medical record having medical data regarding a first patient has been modified;
responsive to determining that the first electronic medical record has been modified:
making, by the computer system based on the first electronic medical record, a first determination that the first patient:
had been previously diagnosed with CKD and is associated with GFR measurements less than a threshold value,
had previously undergone a kidney transplant,
had previously undergone a renal dialysis procedure,
has not had acute kidney failure,
had previously been diagnosed with another type of kidney disease, and/or
is associated with two or more GFP measurements less than the threshold value within a threshold period of time,
responsive to making the first determination, making, by the computer system based on the first electronic medical record, a second determination that the first patient does not satisfy one or more exclusion criteria, and responsive to making the second determination, making, by the computer system based on the first electronic medical record, a third determination that the first patient:
has type 2 diabetes, and/or
has hypertension; and responsive to making the third determination, automatically determining, by the computer system, that the first patient has CKD.

7. A system comprising:
one or more processors; and
one or more non-transitory computer readable media storing instructions that are operable when executed by the one or more processors to perform operations comprising:
obtaining electronic medical records having medical data regarding a plurality of patient, the medical data comprising, for each patient:
an indication if the patient had been previously diagnosed with CKD,
an indication if the patient had previously had acute kidney failure,
an indication if the patient had previously undergone a kidney transplant,
an indication if the patient had previously undergone a renal dialysis procedure,
an indication if the patient had previously been diagnosed with another type of kidney disease,
one or more glomerular filtration rate (GFR) measurements associated with the patient,
an indication if the patient has type 2 diabetes, and
an indication if the patient has hypertension;
automatically identifying a first subset of patients among the plurality of patients, wherein identifying the first subset of patients comprises identifying, based on the electronic medical records, one or more patients of the plurality of patients that:
had been previously diagnosed with CKD and are associated with GFR measurements less than a threshold value,
had previously undergone a kidney transplant,
had previously undergone a renal dialysis procedure,
have not had acute kidney failure,
had previously been diagnosed with another type of kidney disease, and/or are associated with two or more GFP measurements less than the threshold value within a threshold period of time,
automatically identifying a second subset of patients among the first subset of patients, wherein identifying the second subset of patients comprises identifying, based on the electronic medical records, one or more patients of the first subset of patients that does not satisfy one or more exclusion criteria;
automatically identifying a third subset of patients among the second subset of patients, wherein identifying the third subset of patients comprises identifying, based on the electronic medical records, one or more patients of the second subset of patients that:
have type 2 diabetes, and/or
have hypertension;
automatically determining that the third subset of patients has CKD;

determining that a first electronic medical record having medical data regarding a first patient has been modified;

responsive to determining that the first electronic medical record has been modified:
making, based on the first electronic medical record, a first determination that the first patient:
had been previously diagnosed with CKD and is associated with GFR measurements less than a threshold value,
had previously undergone a kidney transplant,
had previously undergone a renal dialysis procedure,
has not had acute kidney failure,
had previously been diagnosed with another type of kidney disease, and/or is associated with two or more GFP measurements less than the threshold value within a threshold period of time,
responsive to making the first determination, making, based on the first electronic medical record, a second determination that the first patient does not satisfy one or more exclusion criteria, and
responsive to making the second determination, making, based on the first electronic medical record, a third determination that the first patient:
has type 2 diabetes, and/or
has hypertension; and
responsive to making the third determination, automatically determining, by the computer system, that the first patient has CKD.

8. The system of claim 7, wherein automatically determining that the third subset of patients has CKD includes determining whether each patient of the third subset of patients has diabetic CKD, has diabetic/hypertensive CKD, or has hypertensive CKD.

9. One or more non-transitory computer readable media storing instructions that are operable when executed by one or more processors to perform operations comprising:
obtaining electronic medical records having medical data regarding a plurality of patients, the medical data comprising, for each patient:
an indication if the patient had been previously diagnosed with CKD,
an indication if the patient had previously had acute kidney failure,
an indication if the patient had previously undergone a kidney transplant,
an indication if the patient had previously undergone a renal dialysis procedure,
an indication if the patient had previously been diagnosed with another type of kidney disease,
one or more glomerular filtration rate (GFR) measurements associated with the patient,
an indication if the patient has type 2 diabetes, and
an indication if the patient has hypertension; and
automatically identifying a first subset of patients among the plurality of patients, wherein identifying the first subset of patients comprises identifying, based on the electronic medical records, one or more patients of the plurality of patients that:
had been previously diagnosed with CKD and are associated with GFR measurements less than a threshold value,
had previously undergone a kidney transplant,
had previously undergone a renal dialysis procedure,
have not had acute kidney failure,
had previously been diagnosed with another type of kidney disease, and/or are associated with two or more GFP measurements less than the threshold value within a threshold period of time, automatically identifying a second subset of patients among the first subset of patients, wherein identifying the second subset of patients comprises identifying, based on the electronic medical records, one or more patients of the first subset of patients that does not satisfy one or more exclusion criteria;

automatically identifying a third subset of patients among the second subset of patients, wherein identifying the third subset of patients comprises identifying, based on the electronic medical records, one or more patients of the second subset of patients that:
have type 2 diabetes, and/or
have hypertension;

automatically determining that the third subset of patients has CKD;

determining, by the computer system, that a first electronic medical record having medical data regarding a first patient has been modified;

responsive to determining that the first electronic medical record has been modified:
making, based on the first electronic medical record, a first determination that the first patient:
had been previously diagnosed with CKD and is associated with GFR measurements less than a threshold value,
had previously undergone a kidney transplant,
had previously undergone a renal dialysis procedure,
has not had acute kidney failure,
had previously been diagnosed with another type of kidney disease, and/or
is associated with two or more GFP measurements less than the threshold value within a threshold period of time, responsive to making the first determination, making, based on the first electronic medical record, a second determination that the first patient does not satisfy one or more exclusion criteria, and responsive to making the second determination, making, based on the first electronic medical record, a third determination that the first patient:
has type 2 diabetes, and/or
has hypertension; and responsive to making the third determination, automatically determining, by the computer system, that the first patient has CKD.

10. The one or more non-transitory computer readable media of claim 9, wherein the step of automatically determining that the third subset of patients has CKD includes determining whether each patient of the third subset of patients has diabetic CKD, has diabetic/hypertensive CKD, or has hypertensive CKD.

* * * * *